(12) United States Patent
Ho

(10) Patent No.: US 9,546,386 B2
(45) Date of Patent: Jan. 17, 2017

(54) GLUCOSE AND XYLOSE CO-FERMENTING MICROORGANISM THAT EXPRESSES ACTIVE GLUCOAMYLASE

(71) Applicant: Tekkware, Inc., South Bend, IN (US)

(72) Inventor: Nancy W. Y. Ho, West Lafayette, IN (US)

(73) Assignee: Tekkware, Inc., South Bend, IN (US)

( * ) Notice: Subject to any disclaimer, the term of this patent is extended or adjusted under 35 U.S.C. 154(b) by 0 days.

(21) Appl. No.: 14/839,372

(22) Filed: Aug. 28, 2015

(65) Prior Publication Data

US 2016/0060659 A1    Mar. 3, 2016

Related U.S. Application Data

(60) Provisional application No. 62/045,454, filed on Sep. 3, 2014.

(51) Int. Cl.
| | | |
|---|---|---|
| *C12P 7/10* | (2006.01) | |
| *C07C 31/08* | (2006.01) | |
| *C12N 9/12* | (2006.01) | |
| *C10L 1/02* | (2006.01) | |
| *C12N 9/34* | (2006.01) | |
| *C12N 9/04* | (2006.01) | |
| *C12N 1/18* | (2006.01) | |
| *C12N 1/22* | (2006.01) | |

(52) U.S. Cl.
CPC .. *C12P 7/10* (2013.01); *C10L 1/02* (2013.01); *C12N 1/18* (2013.01); *C12N 1/22* (2013.01); *C12N 9/0006* (2013.01); *C12N 9/1205* (2013.01); *C12N 9/2428* (2013.01); *C10L 2200/0469* (2013.01); *C10L 2290/26* (2013.01); *C12Y 101/01* (2013.01); *C12Y 207/01017* (2013.01); *C12Y 302/01003* (2013.01)

(58) Field of Classification Search
None
See application file for complete search history.

(56) References Cited

U.S. PATENT DOCUMENTS 5,789,210 A * 8/1998 Ho ................ C12N 9/0006
435/163

FOREIGN PATENT DOCUMENTS

WO    WO9742307    * 11/1997

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report and Written Opinion for PCT/US2015/047625, mailed Dec. 15, 2015, 14 pages.
Voronvsky et al, Development of strains of the thermotolerant yeast *Hansenula polymorpha* capable of alcoholic fermentation of starch and xylan, Metabolic Engineering 11 (2009), pp. 234-242.

* cited by examiner

*Primary Examiner* — Christian Fronda
(74) *Attorney, Agent, or Firm* — Louis Wu

(57) ABSTRACT

Provided are microorganisms, e.g., the *Saccharomyces* yeast, that have been made able to co-ferment xylose sugar-obtained from hydrolyzing plant cellulosic biomass form trees, grasses, straws, etc., with glucose that can be obtained from hydrolyzing either edible feedstocks such as starch, cane sugar, etc. or from hydrolyzing cellulose from various types of non-edible cellulosic biomass. The microorganisms are also capable of expressing an amylase, e.g., glucoamylase, having nonnegligible enzymatic activity, capable of producing glucose from oligo- or polysaccharides obtained by treating soluble starch with α-amylase. In some embodiments, nucleotidic material is provided comprising genes actively expressing xylose reductase, xylitol dehydrogenase and xylulokinase as well as an active gene expressing glucoamylase. Vectors and other compositions of matter are provided as.

8 Claims, 5 Drawing Sheets

| GLUCOAMYLASE ACTIVITY OF VARIOUS STRAINS OF S. CEREVISIAE YEAST | |
| --- | --- |
| STRAIN ID | GLUCOAMYLASE ACTIVITY (µG/MIN/ML) |
| Commercially available | Negligible |
| ATCC strain 4124 (Unmodified) | Negligible |
| 424A(LNH-ST) | 3.0 µg/min/ml |
| 424A (LNH-ST)-GA | 25 µg/min/ml |
| 424A (LNH-ST)-Gal-GA | 45 µg/min/ml |

FIG. 2

GLUCOSE AND XYLOSE CO-FERMENTING MICROORGANISM THAT EXPRESSES ACTIVE GLUCOAMYLASE

CROSS REFERENCE TO RELATED APPLICATIONS

This patent application claims priority to U.S. Patent Application Ser. No. 62/045,454, entitled "XYLOSE AND GLUCOSE CO-FERMENTING MICROORGANISM THAT EXPRESSES ACTIVE GLUCOAMYLASE," filed Sep. 3, 2014 by inventor Nancy W. Y. Ho, the disclosure of which is incorporated by reference in its entirety.

BACKGROUND OF THE INVENTION

Ethanol and other alcohols may be used to fuel automobiles and other machinery powered by internal combustion engines, either as a neat fuel or as a blend with gasoline at various concentrations. For example, the use of oxygenated materials in gasoline can reduce the emission of carbon monoxide, a harmful pollutant, into the air. Among several oxygenates currently used for boosting the oxygen content of gasoline, ethanol has the highest oxygen content. The United States Environmental Protection Agency (EPA) has shown that gasoline blended with 10% ethanol reduces carbon monoxide emissions by about 25% to 30%.

Up to now, the feedstock used for the production of industrial alcohol by fermentation contain six carbon sugars and starches such as that from sugar cane, beets, corn or other edible crops. However, these agricultural crops have generally been too expensive to be used as feedstock for the large-scale production of fuel ethanol. In addition, the edible crops can only be produced in rich farm land and are in limited supply. Since the population of the world continues to increase, crops are needed to feed the people.

Plant biomass is an attractive feedstock for ethanol-fuel production by fermentation because it is renewable, and available at low cost and in large amounts around the world. The major fermentable sugars from cellulosic materials are six-carbon sugars such as glucose and five-carbon sugars such as xylose. Glucose and xylose are the major sugars present in all types of cellulosic biomass (trees, grasses, straws, etc.) with the ratio of glucose to xylose being approximately 2 to 1. The most desirable fermentations of cellulosic materials would, of course, completely convert both glucose and xylose to ethanol. Unfortunately, even now there is not a single natural known microorganism capable of fermenting both glucose and xylose effectively and efficiently to ethanol.

Some yeasts, particularly of the genus *Saccharomyces*, have traditionally been used for fermenting glucose-based feedstock to ethanol, and they are still the best microorganisms for converting glucose to ethanol. However, these glucose-fermenting yeasts have been found not only unable to ferment xylose but also unable to use the pentose sugar for growth. Nevertheless, glucose-fermenting yeasts can use xylulose for growth and fermentation, albeit with varying efficacy. For example, *S. cerevisiae* ferments xylulose very poorly while species of *Schizosaccharomyces* does so quite effectively. However, the latter yeast has not been used traditionally for ethanol production, particularly for large scale industrial ethanol (fuel ethanol) production.

Even though the glucose-fermenting yeasts are unable to use xylose both for growth and fermentation, there are many other natural yeasts that can use xylose for growth aerobically, but they cannot ferment xylose efficiently to ethanol. Particularly, these xylose-fermenting yeasts also ferment glucose very poorly to ethanol. These xylose-utilizing yeasts rely upon two enzymes—xylose reductase and xylitol dehydrogenase—to convert xylose to xylulose. These yeasts are different from most bacteria which rely on a single enzyme—xylose isomerase—to convert xylose directly to xylulose. The yeast xylose reductase and xylitol dehydrogenase also require cofactors for their actions; xylose reductase depends on NADPH as its cofactor and xylitol dehydrogenase depends on NAD as its cofactor. On the contrary, bacterial xylose isomerase requires no cofactor for direct conversion of xylose to xylulose.

Historically, since the early 1970s, efforts were devoted in an attempt to find new yeasts capable of effectively fermenting both glucose and xylose to ethanol in a cost effective manner. However, no ideal yeast able to ferment both glucose and xylose effectively was found by 1980.

Among xylose-fermenting yeasts, three species, *Pachysolen tannophilus, Candida shehatae*, and *Pichia stipitis* have been extensively characterized. *P. stipitis* and *C. shihatae* ferment xylose better than the other xylose-fermenting yeasts. Nevertheless, even the best xylose-fermenting yeasts lack high efficiency in fermenting xylose, and are also highly ineffective in fermenting glucose.

By 1980, scientists worldwide believed that an ideal C5/C6 co-fermenting yeast could be created by using the then-newly developed recombinant DNA techniques to engineer *Saccharomyces* yeast so that the resulting yeast may efficiently ferment sugars extracted from cellulosic biomass. Initial efforts were concentrated on cloning a xylose isomerase gene into yeast to render it capable of converting xylose directly to xylulose without dependence on cofactors. However, these efforts have been unsuccessful initially because the genes encoding various bacterial xylose isomerases are incapable of directing the synthesis of an active enzyme in *S. cerevisiae*.

Subsequently, efforts toward genetically engineering yeasts, particularly *S. cerevisiae*, to ferment xylose have been focused on cloning genes encoding xylose reductase and xylitol dehydrogenase. *S. cerevisiae* and other glucose-fermenting yeasts do not contain any detectable xylose reductase or xylitol dehydrogenase activities, but all seem to contain xylulokinase activity. Thus, the glucose-fermenting yeasts can all ferment xylulose, but do so with varying efficacy.

Initially, researchers have only tried to clone both the xylose reductase and the xylitol dehydrogenase gene in *S. cerevisiae*. However, these genetically engineered yeasts still cannot effectively ferment xylose. For example, these yeasts have been incapable of fermenting more than 2% xylose. In addition, they produce large amounts of xylitol from xylose, which diverts the valuable xylose substrate from the desired fermentation path to ethanol. Nevertheless, this has been changed due to the technologies provided by the following patents: U.S. Pat. Nos. 5,789,210, 7,527,927 and 8,652,772, each to Ho et al. The methods described in these patents have made it possible to develop the glucose/xylose co-fermenting yeast that can effectively co-ferment glucose and xylose to ethanol. The yeasts developed by Ho et al. according to these patented technologies have proven to be particularly efficient for co-fermenting both glucose and xylose to ethanol. The first such glucose and xylose co-fermenting yeast was developed before 1993. The strain was designated as 1400 (LNH-ST). Subsequently, quite a few of such strains were developed by Ho et al., including strain 424A(LNH-ST), which may be abbreviated herein and accompanying drawings as 424A. As shown in FIG. 1, the 424A(LNH-ST) yeast has been proven able to produce high concentrations of ethanol when high concentrations of glucose is available. This is because the 424A(LNH-ST) yeast was developed by selecting the best ethanol producing yeast to develop the glucose/xylose co-fermenting yeast. Sedlak et al. (2004), "Production of Ethanol from Cellulosic Biomass Hydrolysates Using Genetically Engineered *Saccharomyces* Yeast Capable of Cofermenting Glucose and Xylose," APPLIED BIOCHEMISTRY AND BIOTECHNOLOGY, 113-116: 403-16.

Glucoamylase, also known as glucan 1,4-alpha-glucosidase, amyloglucosidase, gamma-amylase, lysosomal alpha-glucosidase, acid maltase, exo-1,4-alpha-glucosidase, glucose amylase, gamma-1,4-glucan glucohydrolase, acid maltase, and 1,4-alpha-D-glucan glucohydrolase, is an enzyme with a system name of 4-alpha-D-glucan glucohydrolase. The enzyme catalyzes the following chemical reaction: hydrolysis of terminal (1->4)-linked alpha-D-glucose residues successively from non-reducing ends of the chains with release of beta-D-glucose. Most forms of the enzyme can rapidly hydrolyse 1,6-alpha-D-glucosidic bonds when the next bond in the sequence is 1,4. Genes that code for the expression of glucoamylase have been cloned into yeasts such as *S. cervisiae*. See, e.g., U.S. Pat. No. 5,422,267 to Yocum et al. Typically, glucoamylase is produced in industrial scale using microorganisms such as *Aspergillus Niger*. Often, glucoamylase is added to speed up fermentation of wort, honey, grape juice, or other fluids or solutions containing sugar.

As discussed in Pretorius et al. (1991), "The Glucoamylase Multigene Family in *Saccharomyces cerevisiae* var. *diastaticus*: An Overview," CRITICAL REVIEWS IN BIOCHEMISTRY AND MOLECULAR BIOLOGY, 26(1):53-76, *S. cerevisiae* has been used widely both as a model system for unraveling the biochemical, genetic, and molecular details of gene expression and the secretion process, and as a host for the production of heterologous proteins of biotechnological interest. The potential of starch as a renewable biological resource has stimulated research into amylolytic enzymes and their substrate range in *S. cerevisiae*. The enzymatic hydrolysis of starch, consisting of linear (amylose) and branched glucose polymers (amylopectin), is catalyzed by α- and βamylases, glucoamylases, and debranching enzymes. Starch utilization in the yeast *S. cerevisiae* var. *diastaticus* depends on the expression of the three unlinked genes, STA1 (chr. IV), STA2 (chr. II), and STA3 (chr. XIV), each encoding one of the extracellular glycosylated glucoamylases isozymes GAI, GAII, or GAIII, respectively. Additional research relating to research pertaining to *S. cerevisiae* can be found in Pugh et al. (1989), "Characterization and localization of the sporulation glucoamylase of *Saccharomyces cerevisiae*," BIOCHIMICA ET BIOPHYSICA ACTA, 994: 200-209.

Despite the concerted and longstanding efforts of numerous researchers, a single organism capable of fermenting in an economically feasible manner biomass containing starch as the sole or main precursor to ethanol (or alcohol), e.g., without needing to add glucoamylase from another source, to replace hydrocarbon fuels such as gasoline has not been achieved. Although certain entities have strived to improve biomass biotechnological productivity, e.g., Mascoma Corporation (Lebanon, N.H.), none have achieved the level of success to meet long-felt industry needs as reflected by subject matter encompassed by the claims below.

Accordingly, there remains a need for such microorganisms and for methods of their preparation and use.

SUMMARY OF THE INVENTION

In a first embodiment, a container containing biomass and a microorganism is provided. The microorganism is capable of fermenting both glucose and xylose-to ethanol. The microorganism is also capable of expressing an amylase, e.g., glucoamylase having nonnegligible (active) enzymatic activity for breaking down glucosic polysaccharides of the biomass.

In another embodiment, nucleotidic material is provided comprising genes encoding xylose reductase, xylitol dehydrogenase and xylulokinase and genes encoding for expressing glucoamylase.

In a further embodiment, a method is provided for obtaining a recombinant yeast which metabolize glucose and/or xylose while expressing glucoamylase. The method may involve introducing nucleotidic material for expressing glucoamylase into a yeast that has genes encoding for glucose and/or xylose fermentation. Alternatively, nucleotidic material encoding for xylose fermentation into a yeast that has a gene encoding for xylose metabolization.

In yet another embodiment, a method is provided for fermenting biomass containing glucose and/or xylose and at least two six-carbon saccharidic unit, e.g., the glucosic unit to ethanol. The method comprising fermenting the biomass with a recombinant yeast, the yeast containing an gene encoding for glucoamylase expression and a yeast having genes encoding for xylose fermentation.

In a still further embodiment, a solution that may be safe for human ingestion. The solution containing alcohol with residue and/or coproduct of biomass fermentation by a microorganism is provided. The microorganism is capable of metabolizing glucosic and/or xylosic material and of expressing glucoamylase having nonnegligible enzymatic activity for breaking down polysaccharides of the biomass. The polysaccharides may contain at least two six-carbon saccharidic unit.

Additional embodiments, features and advantages of the invention will be apparent from the following description.

BRIEF DESCRIPTION OF THE DRAWINGS

FIG. 2 is a table that shows the glucoamylase expressing activity of various strains of the inventive yeast versus other strains of yeast.

DETAILED DESCRIPTION OF THE INVENTION

Definitions and Overview

Figure 1:
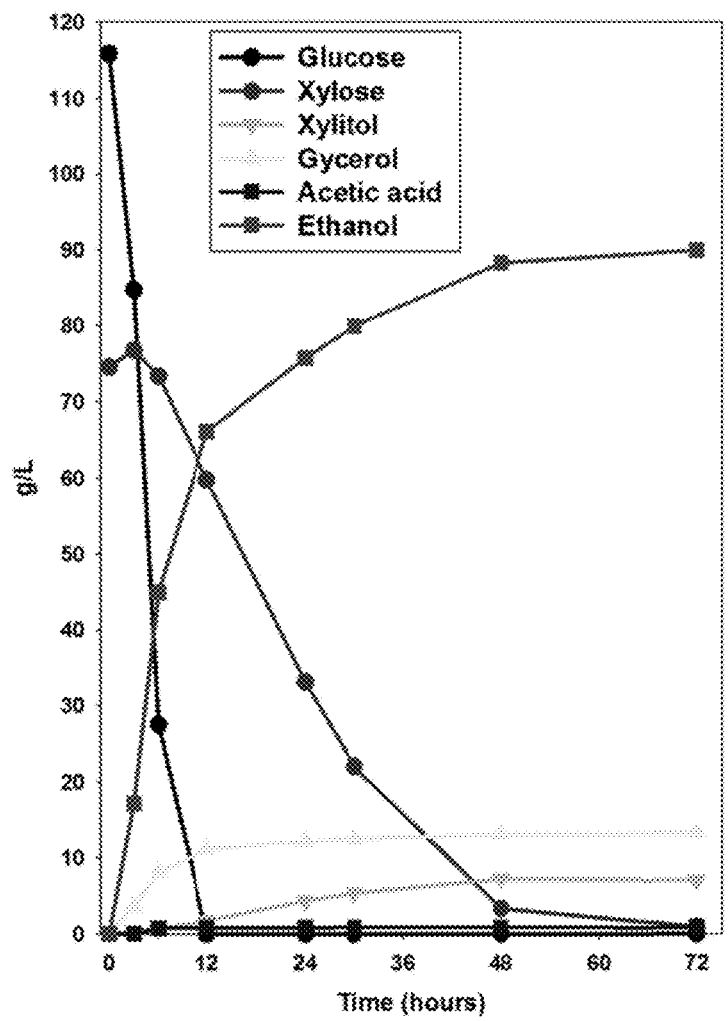
FIG. 1 is a graph that plots the concentration of various compounds as glucosic and xylosic digestion takes place using a typical strain of recombinant yeast, 424A(LNH-ST), engineered to produce ethanol from biomass. Coproducts of such digestion include xylitol, glycerol, and acetic acid.

Before describing the present invention in detail, it should be noted that embodiments of the invention may take the form of a useful process, machine, manufacture, or composition of matter, or any new and useful improvement thereof. It is also to be understood that the invention is not limited to specific species of microorganisms, or whether the invention takes the form of an organism that is classified as fungal, bacterial, or otherwise, as such may vary. It is further to be understood that the terminology used herein is for the purpose of describing particular embodiments only, and is not intended to be limiting.

In addition, as used in this specification and the appended claims, the singular article forms "a," "an," and "the" include both singular and plural referents unless the context clearly dictates otherwise. Thus, for example, reference to "a microorganism" includes a plurality of microorganisms as well as a single microorganism, reference to "a gene" includes a single gene as well as a combination of genes, and the like.

In this specification and in the claims that follow, reference is made to a number of terms that shall be defined to have the following meanings, unless the context in which they are employed clearly indicates otherwise:

The terms "active," and "activity" are used in their ordinary sense to refer to a state characterized by action rather than inertness.

The term "amylase" is used in its ordinary sense to refer to an enzyme that catalyzes the hydrolysis of starch into sugars. For example, the term "glucoamylase" refers to an enzyme that catalyzes the hydrolysis of glucosic material into glucosic sugars.

The term "alcohol" is used in its ordinary sense to refer to any of a class of chemical compounds having the general formula ROH, where R may represent an alkyl group and —OH, a hydroxyl group, as in ethanol, $C_2H_5OH$. Additional examples of alcohols include xylitol, glycerol and other sugar alcohols or polyols.

The term "biomass" is used in its ordinary sense and refers to organic matter, especially plant matter, which can be converted to fuel and is therefore regarded as a potential energy source.

The term "coproduce" is used in its ordinary sense and refers to an incidental product, e.g., something produced during the manufacture or production of something else, often something useful or commercially valuable.

The term "enzyme" is used to refer to any of various proteins, as pepsin, originating from living cells and capable of producing certain chemical changes in organic substances by catalytic action, as in digestion.

The term "efficient" is used in its ordinary sense and is used to describe biological and/or chemical means that achieve improved productivity with minimum wasted time, effort, and/or expense. For example, an efficient biochemical process carried out with the invention effects greater productivity relative to a comparable biochemical process that is inefficient in nature. The term is to be interpreted in context in a manner such that the claims encompass only validly patentable subject matter. For example, most living organisms of the invention be kept at a temperature of about 0° C. to about 70° C. For the microorganism of the invention, a fermentation temperature range of about 25° C. to about 35° C. is typically preferred. Optimally, a temperature range of about 28° C. to about 32° C. may be used, keeping in mind that a certain amount of deviation may be permitted. In any case, specific fermentation temperatures and ranges thereof may vary depending on the requirements associated with efficient commercial production, e.g., of ethanol and/or other organic compounds of interest. For example, certain processes may involve different temperature profiles over time, so as to ensure appropriate production of glucoamylase and other enzymes without contributing to microorganism health problems associated with temperature and unwanted by-products.

The terms "gene," "genetic material," and the like are used to refer a molecular unit of heredity of a living organism. The terms are typically used to identify some stretches of DNA or RNA that code for a peptidic material such as an enzyme.

The terms "glucose," "glucosic," "glucosidic," "C6," and the like are used in their ordinary biochemical sense and refer to a sugar, $C_6H_{12}O_6$, having several optically different forms, the common dextrorotatory form (dextroglucose, or -glucose) occurring in many fruits, animal tissues and fluids, etc. Exemplary glucosic materials include levoglucose, dextrose, maltose, sucrose, starches, and starch syrups such as corn syrup.

The prefix "micro" refers to items having dimensions on the order of micrometers or having volumes on the order of microliters or somewhat less in size or dimensions. Thus, for example, the term "microorganism" refers to an organism, comprising a single cell, several cells, tens of cells, or greater than one hundred cells, wherein a representative dimension of the organism is about on the order of microns or submicrons. The largest dimension of a microorganism is no greater than about 1 millimeter. Other terms containing the prefix "micro" are to be construed in a similar manner.

The term "nonnegligible" generally refers to something substantial, significant or nontrivial, e.g., something not so small, trifling, or unimportant that it may safely be neglected or disregarded. As used herein, the term should be construed in an economic, industrial, scientific, technological, and/or biological sense.

For example, it is imaginable a naturally occurring microorganism may through natural selection without any human intervention be able to coferment glucose and xylose while expressing a nonnegligible amount of glucoamylase. However, such production of glucoamaylase does not necessarily result in efficient C5 and C6 cofermentation. In any case, the claims below are not intended to cover such a microorganism to an extent that would render the claims invalid under 35 U.S.C. §101 or related case law. See, e.g., Association for Molecular Pathology v. Myriad Genetics, 569 U.S. 12-398 (2013) (Slip Op.), http://www.supremecourt.gov/opinions/12pdf/12-398_1b7d.pdf.

As a related matter, the term "nonnegligible enzymatic activity" when used to describe glucoamylase expression should generally be construed in a quantitatively measurable sense. For example, yeast may express glucoamylase in any of a number of forms, active or not-so active. While not wishing to be bound by theory, it is believed that glucoamylase activity may be dependent on whether the glucoamylase is bound within intracellular location, e.g. attached to the yeast's cell wall or membrane or whether the enzyme is secreted to the yeast cultural medium. Thus, a quantitative measure of whether a yeast's enzymatic activity is nonnegligible is to measure the concentration of ethanol over time in a culture medium containing the yeast and oligosaccharides as the feedstock.

The terms "nucleotide," "nucleotidic," and the like refer to organic molecules that serve as the monomers or subunits of nucleic acids like DNA (deoxyribonucleic acid) and RNA (ribonucleic acid). The building blocks of nucleic acids, nucleotides are composed of a nitrogenous base, a five-carbon sugar (ribose or deoxyribose) and at least one phosphate group.

The prefix "oligo" as in "oligomer" is used in its ordinary sense to refer to a short" polymer that has only a few monomeric units. Thus, an "oligosaccharide" is a polysaccharide with relatively few saccharidic units.

The terms "peptide," "peptidic," and the like refer to a compound containing at least one amino acid, more typically two or more amino acids in which the carboxyl group of one acid is linked to the amino group of the other.

A "plasmid" is a small DNA molecule that is physically separate from, and can replicate independently of, chromosomal DNA within a cell. Commonly found as small circular, double-stranded DNA molecules in microorganisms, plasmids carry genes that may benefit survival of an organism.

The term "promotor" may refer to a region of DNA that initiates transcription of a particular gene.

The term "recombinant" is used to refer to matter that is of, relating to, or involved in genetic recombination, particularly by using scientific techniques carried out in vitro.

The term "residue" is used to refer something left over, e.g., something that remains after a process involving the removal of part of the original has been completed.

The terms "saccharide," "saccharidic," and the like are used in their ordinary sense to refer to an organic compound containing a sugar, e.g., a simple sugar such as a monosaccharide or an ester of sucrose, or a polysaccharide like starch.

A "vector" is a DNA molecule used in molecular cloning as a vehicle to artificially carry foreign genetic material into another cell, where the genetic sequence of the DNA molecule can be replicated and/or expressed.

The term "xylose," "xylosic," "C5," and the like are used in their ordinary sense to refer to a pentose sugar, $C_5H_{10}O_5$, derived from xylan, straw, corncobs, etc. For example, xylulose is a type pentose sugar. The term "xylosic" when applied to a molecule does not necessarily exclude glucosic molecules and vice versa. For example, it is theoretically possible for a polysaccharide to have a chain structure that includes monomeric units, some of which being xylosic while others of which being glucosic in structure.

The invention relates to a microorganism capable of fermenting biomass, e.g., in the form of a fluid such as a liquid and/or solution. Some microorganisms by themselves may be capable of fermenting xylosic material and of expressing and/or secreting glucoamylase having nonnegligible enzymatic activity for breaking down glucosic polysaccharides of the biomass. Typically, the microorganism has nucleotidic material traceable to a man-made recombinant process. The microorganism may be a yeast, e.g., of the genus *Saccharomyces*, that ferments glucose to ethanol. However, other microorganisms such as those discussed in U.S. Pat. No. 5,789,210 to Ho et al. The microorganism may be in diploid, polyploid, or a haploid state for asexual or sexual reproduction, respectively.

In addition, the invention relates to recombinant *Sacchromyces cerevisiae* yeast nucleotidic material comprising genes encoding xylose reductase, xylitol dehydrogenase and xylulokinase and genes encoding for expressing glucoamylase. For example, the material may be present in the form of a recombinant yeast which ferments xylose or glucose or both glucose and xylose to ethanol while also expressing glucoamylase. The yeast may be formed using a vector to introduce nucleotidic material for xylose fermentation into a yeast that expresses glucoamylase. Alternatively, the yeast may be formed by using a vector to introduce nucleotidic material for glucoamylase expression into a yeast that has genes encoding for xylose fermentation. Other ways to form yeasts of the invention may be formed via other techniques as well. Furthermore, the invention provides a method for fermenting biomass containing at least two six-carbon saccharidic unit to ethanol. The method involves fermenting biomass with a recombinant yeast, the yeast capable of fermenting glucose efficiently to ethanol. The yeast contains a gene or genes encoding enzymes for xylose fermentation and a gene encoding for expression of glucoamylase. As a result, a solution containing alcohol and other residue or products of biomass fermentation may be produced. Ordinarily, the solution is safe to be used as a transportation fuel, perhaps even for human and animal ingestion, e.g., via eating, drinking, inhaling, injection, or some other means.

Recombinant Genes

In general, any of a number of recombinant genes may be used to carry out the invention. Exemplary genes associated with glucoamylase expression are discussed in Yocum et al. Three structural genes are known for expressing glucoamylase, STA, DEX, and SGA. Glucoamylase genes from other microorganisms, such as from *Aspergillus* species, can also be used for making yeast to produce glucoamylase in yeast.

In general, *Saccharomyces* yeasts only express one of the glucoamylase genes during mating, and the enzyme is not secreted. In contrast, yeasts may contain the other two genes and may therefore be able to secrete the enzyme.

As for other dispersed genes for sugar utilization (MAL, maltose fermentation; SUC, sucrose fermentation), the STA genes comprise a small gene family. STA1 and STA2 are highly homologous to each other as well as to the 'cryptic sta' or SGA gene, and it has been suggested that the STA genes arose from the ancestral SGA form by genomic rearrangement. The STA+ phenotype also requires the presence of a recessive allele of another gene, STA0 (also called INH1), whose function is presently unknown.

Comparison of the STA1 and SGA nucleotide sequences has revealed that the carboxy-terminal portions of these molecules are nearly identical, and that both contain potential sites for N-linked glycosylation. STA1 contains, in addition, a serine and threonine-rich amino terminal domain which presumably provides sites for the extensive O-glycosylation which is observed in vivo as well as secretory information for the molecule.

Exemplary genes associated with xylosic fermentation are discussed in U.S. Pat. No. 5,789,210 to Ho et al. and include XR, XD and XK genes. Such genes are well known to occur in a wide variety of microorganisms and, in fact, as discussed hereinabove, numerous XR, XD and XK genes have been identified and isolated. The particular source of these genes is not critical to the broad aspects of this invention; rather, any nucleotidic encoding peptidic enzymes having xylose reductase activity (the ability to convert D-xylose to xylitol with NADPH or NADH as cofactor), xylitol dehydrogenase activity (the ability to convert xylitol to D-xylulose with + as cofactor), or xylulokinase activity (the ability to convert D-xylulose to D-xylulose-5-phosphate) will be suitable. These genes may be obtained as naturally-occurring genes, or may be modified, for example, by the addition, substitution or deletion of bases to or of the naturally-occurring gene, so long as the encoded protein still has the enzyme activities encoded by the XR, XD or XK genes. Similarly, the genes or portions thereof may be synthetically produced by known techniques, again so long as the resulting DNA encodes a protein exhibiting the desired xylose reductase, xylitol dehydrogenase, or xylulokinase activity.

As examples, suitable sources of XR and XD genes include xylose-utilizing yeasts such as *Candida shehatae, Pichia stipitis, Pachysolen tannophilus*, suitable sources of XK genes include the above-noted xylose-utilizing yeasts, as well a xylose non-utilizing yeasts such as those from the genus *Saccharomyces*, e.g. *S. cerevisiae*, the genus *Schizosaccharomyces*, e.g. *Schizosaccharomyces pombe*, and bacteria such as *Escherichia coli, Bacillus* species, *Streptomyces* species, etc. Genes of interest can be recovered from these sources utilizing conventional methodologies. For example, hybridization, complementation or PCR techniques can be employed for this purpose.

Exemplary Process

In any case, any of a number of known recombinant processes or methods may be used to introduce exogenous genetic material into microorganism of the invention. Such processes are not limited by any particular type of vector, as such may vary. Exemplary suitable processes and methods are discussed in Yocum et al. and Ho et al. Exemplary vector types suitable for use with the invention include plasmid vectors, binary vectors, cloning vectors such as those for integrating genes into a host chromosome, expression vectors, shuttle vectors, and viral vectors.

Thus, microorganisms of the invention may be produced by a process that involves transforming cells of the microorganism with a replicative and integrative plasmid comprising an autonomous replicating sequence, exogenous nucleotidic material, and a selection marker. The transformed cells are replicated to produce a number of generations of progeny cells. The process also involves selecting for cells which include the selection marker, and promoting the retention of the replicative and integrative plasmid in subsequent generations of the progeny cells to produce progeny cells having multiple integrated copies of the exogenous nucleotidic material. Optionally, the process further comprises: repeatedly replicating the progeny cells to produce a number of generations of progeny cells in the absence of selection for cells which include the selection marker, so as to promote the loss of the plasmid in subsequent generations of progeny cells; and recovering the cells each containing multiple copies of the exogenous nucleotidic material integrated into its endogenous nucleotidic material.

Selection markers may vary. For example, antibiotic resistance genes are often to be used as selection markers. However, using antibiotics as selection markers also has serious drawbacks such as too expensive for large scale production and they may induce antibiotic resistant lethal bacteria. The substrates need the cloned genes for their use can also be used as the selection markers for cloning the desired gene(s).

The resulting recombinant organism may include a large number of copies of the exogenous nucleotidic material integrated into endogenous nucleotidic material, for example, more than 10 copies. The resulting microorganism may also exhibit a fermentation activity that does not decrease after culture in non-selective medium for 20, 40, several hundred, or more generations.

The exogenous nucleotidic material may be integrated at reiterated DNA sequences. Such sites may be non-transcribed sites. The non-transcribed reiterated DNA sequences such as the 5S DNA The exogenous nucleotidic material may be fused to non-glucose-inhibited promoters and the yeast simultaneously ferments glucose and xylose to ethanol.

It should be noted that the invention is not necessarily limited to intentional recombinant methods known in the art. Accidental formation of a microorganism having genes that code for glucoamylase expression and xylosic digestion may occur. For example, the original strain of yeast identified as "unmodified laboratory yeast," which has been used for the development of the 424A(LNH-ST) yeast, the 4124 strain, in the table set forth in FIG. 2, as described below, had been found to express little or no glucoamylase. It has now been discovered that the same strain of yeast may, through mutation or some other mechanism, unexpectedly exhibit substantial glucoamylase expression.

Such an unexpected glucoamylase expression was discovered after a number of processes. A first process involved the inventor modifying the yeast to co-ferment glucose and xylose to ethanol. The resulting yeast was named the 424A (LNH-ST) yeast. An additional process involved culturing the 424A(LNH-ST) yeast as a seed culture. A further process involved using the 424A(LNH-ST) yeast for producing ethanol from cellulosic sugars (sugars obtained from hydrolyzing cellulosic biomass from trees, grasses, straws, etc.). It is believed that one or more of these processes may have contributed to the unexpected expression of the original yeast GA gene in producing nonnegligible glucoamylase that contributed to greater effectiveness and efficiency associated with ethanol production.

Culturing and Preserving Conditions

A. Avoid Keeping the Seed Culture on Slants or Plates

One should avoid keeping the seed culture on slants or plates. It should be kept in a 300 ml shaker flask at 4° C. The seed culture can be kept for 3 months at 4° C. Every 3 months, one or more flasks of fresh seed culture should be prepared as needed (following the procedure below for culturing the cells). The seed culture can be transferred and kept as described above even for years so long as the fermentation results remain the same. Nevertheless, from time to time (every six months), a new batch of cultures should be prepared for long-term storage at −70° C.

It is better not to spread the culture on plates to be stored as single colonies. Instead, it is recommended that the culture be maintained as liquid culture. When new seed cultures are made by transferring an aliquot of the existing culture to grow the new seed culture under the selected conditions, the more efficient cells for the intended purpose may be selected and enriched. As such, the culture should not only remain to be effective for the intended purpose and even become more effective for the intended purposes to give good fermentation performance.

B. Preparing Stock Culture for Long Term Preservation

To prepare stock culture for cryopreservation, pipet 0.9 ml freshly cultured seed culture and 0.9 ml 50% sterilized glycerol into each of 2.0 ml cryogenic vials. Mix the cell culture with the glycerol solution well and dip the tubes into a thick dry ice/ethanol bath. Store the tubes containing the frozen cultures in a −70° C. (or lower) freezer.

C. Culture Media

Two kinds of media are routinely used: YEPX or YEPD for culturing, maintaining, and long term preserving the glucose/xylose or C5/C6 co-fermenting yeast. YEPX is used for constructing, maintaining, and preserving the yeast that also contains the externally cloned glucoamylase gene. YEPX contains 1% yeast extract, 2% peptone, and 2% the selection marker xylose used for cloning and maintaining the glucoamylase gene to be used for culturing the seed culture and for long-term preservation of the culture at −70° C. YEPD contains 1% yeast extract, 2% peptone, and 2% glucose, and is used for pre-growing yeast for fermentation.

YEPX, or YEPD is essentially YEP plus 2% a specific sugar. YEP can be prepared in any clean flask so long as the size is appropriate for the final YEPD and/or YEPX needed. An appropriate volume of YEP is first measured and then transferred into the flask that will be used for culturing the cells. For example, if a 300 ml flask (preferably equipped with a side arm for use with a Klett colorimeter to follow cell growth) is to be used for cultivation of the cells either for seed culture or for fermentation, 100 ml of the YEP should be transferred into the flask. The flask is then plugged with either a cotton or foam plug and then sterilized in an autoclave at 121° C. for 20 minutes. Many such flasks can be prepared ahead of time, if they are needed frequently. The flasks can be kept on a shelf or in a cabinet at room temperature or in a refrigerator until they are used. However, the medium in the flask should be examined by lightly swirling it and inspecting it by eye to check for the growth of any contaminates before use. If the flask containing the sterilized YEP is used for culturing the seed culture, 4 ml of sterilized 50% xylose (50 g in 100 ml water) is added to the flask under sterilized conditions to make the final xylose concentration of the resulting YEPX close to 2%. If the flask containing 100 ml of sterilized YEP is used for fermentation, 4 ml of sterilized 50% glucose (prepared the same way as the 50% xylose) should be added under the same sterile conditions.

D. Culturing Temperature and Time

The cells should be cultured at 28-30° C. overnight in proper medium and at least for 16 hrs in a shaker at suitable rpm such as 200 rpm until the optical density is around 400 KU (Klett units) or higher (e.g., 22-26 $OD_{600}$).

E. Seed Culture Propagation

Several media may be used in seed culture propagation. In turn, the seed culture may be used to ferment glucose (or to co-fermenting glucose and xylose) to ethanol while producing glucoamylase. For example, to produce a seed culture that facilitates glucoamylase production, 2-4 ml of a yeast culture containing, e.g., 424A(LNH-ST), 424A(LNH-ST)-GA or another suitable GTA yeast, may be inoculated into a 300 ml flask containing 100 ml YEPG. The YEPG cultured seed culture may then be propagated in a medium containing corn mash provided by any corn ethanol producer. In turn, ethanol can then be produced from corn mash or starch treated with α-amylase or oligosaccharides. As described above, fermentation should be carried out the best at 28-32° C. As discussed below, an exemplary protocol is set forth below for fermenting corn mash.

F. Testing the Seed Culture

For testing the seed culture for 424A(LNH-ST) or other glucose or xylose fermenting yeast that contains, for example, the natural and/or cloned glucoamylase gene actively producing glucoamylase, no special medium is needed, and the medium for culturing 424A(LNH-ST) or for culturing other yeast or other microorganisms is sufficient. For culturing 424A(LNH-ST) able to produce the natural yeast glucoamylase is 2-4 ml of the freshly prepared seed culture should be inoculated into a 300 ml flask containing 100 ml sterilized YEPD or YEPX and incubated in a 28-30° C. shaker until the density of the culture is over 400 KU.

Using standard methods for assaying (or analyzing) the enzyme activity, very little glucoamylase activity is typically found in the cultural medium itself. However, yeast such as 424A(LNH-ST) that produces the natural glucoamylase have been observed to ferment feedstock such as corn mash that contains oligosaccharides obtained from treating starch with alpha-amylase to ethanol. This observation indicates that the enzymes (glucoamylase) produced by the yeast is not secreted into the cultural media, but that the enzymes can nevertheless help to degrade the oligosaccharides present in corn mash to glucose. In turn, glucose is fermented by the yeast to produce ethanol.

For fermenting corn mash by the glucose/xylose co-fermenting yeast such as 424A(LNH-ST), the yeast cells are growing in corn ethanol producers' medium to more than 400-450 KU or OD 22-26. The cells are then centrifuged and transferred to flasks containing enough corn mash sufficient for producing more than 16% ethanol. How much ethanol the yeast can produce in 60-72 hours that will be a direct measure on how much glucoamylase the yeast can provide. It turns out the 424A(LNH-ST) yeast can produce at least 14-16% g/l ethanol within 60 to 72 hour from the corn mesh produced by different companies that are using corn as the feedstock to produce ethanol. For using the 424A(LNH-ST) yeast to ferment corn mesh, the flask should be covered with three layers of Saran wrap (or equivalent strong plastic film) over the plug. The saran wrap should fully encompass the plug and is tightly bound to the flask with three to four strong rubber bends to limit the air flowing into the flask. This ensures that the contents within the flask are at least under micro-aerobic conditions, if not totally anaerobic. The flask is then incubated in the shaker for fermentation to proceed. 1 ml samples are taken from the flask under sterile conditions and transferred to a 1.5 ml Eppendorf tube at 0, 3, 6, 12, 24, 36, 48 hrs or longer, but not more than 72 hours. The cells in the sample tubes will be spun down and the supernatant in each sample tube will be transferred into another properly labeled Eppendorf tube (do not need to transfer every drop of the supernatant but make sure no cells are transferred). These tubes are then kept in a freezer until the samples can be analyzed by HPLC. The HPLC is carried out as described by the conditions provided.

Figure 3:
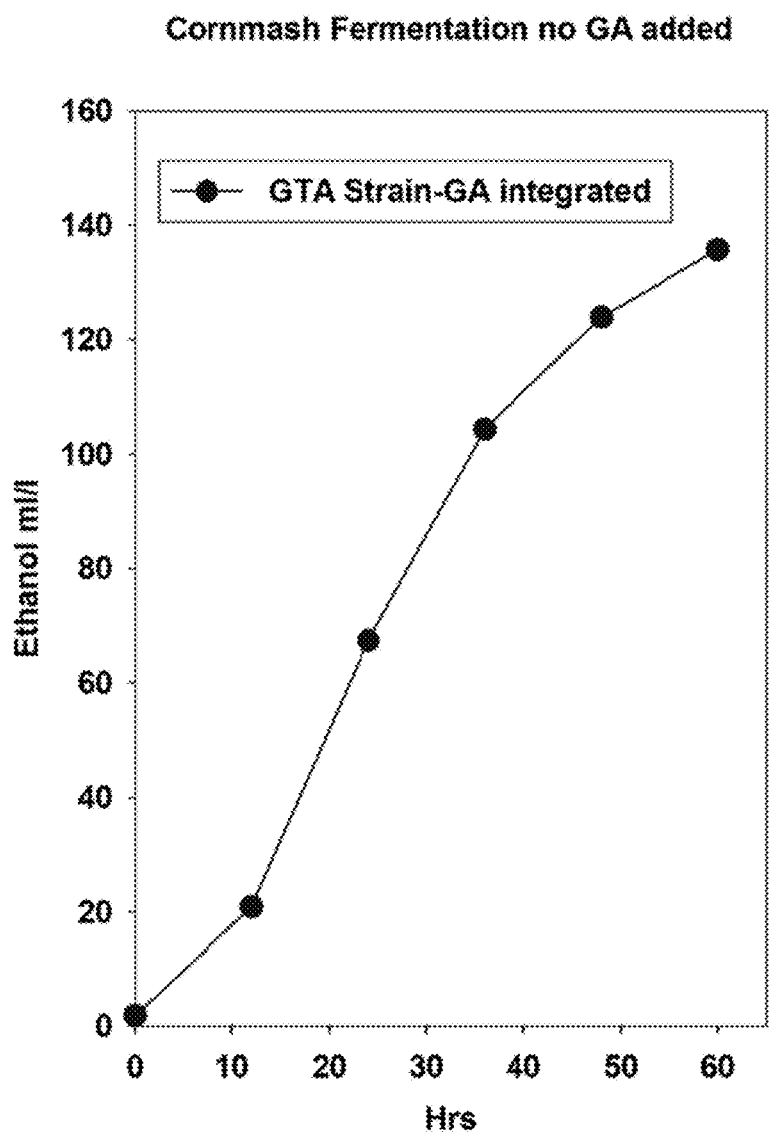
FIG. 3 is a graph that plots the production of ethanol over time via fermentation of corn mash by recombinant yeast (GTA strain 424A(LNH-ST) with GA integrated) without added glucoamylase.
Figure 4:
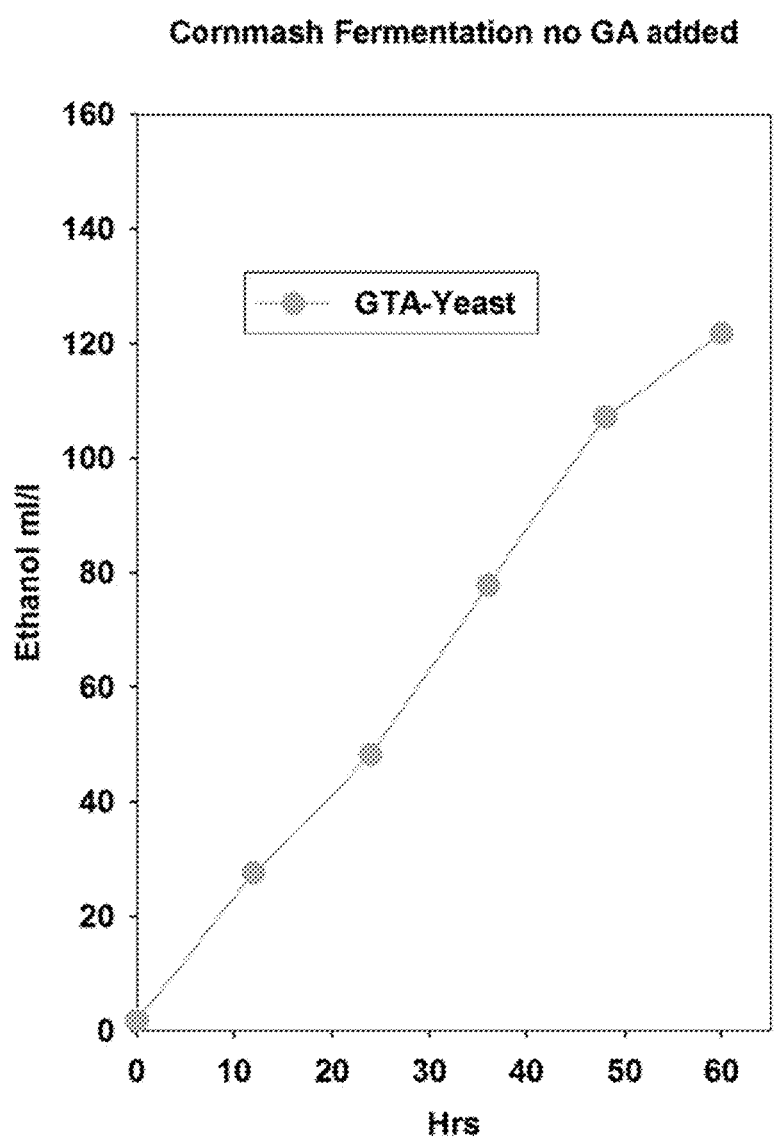
FIG. 4 is a graph that plots the production of ethanol over time via fermentation of corn mash by recombinant yeast (GTA yeast strain 424A(LNH-ST)) without added glucoamylase.
Figure 5:
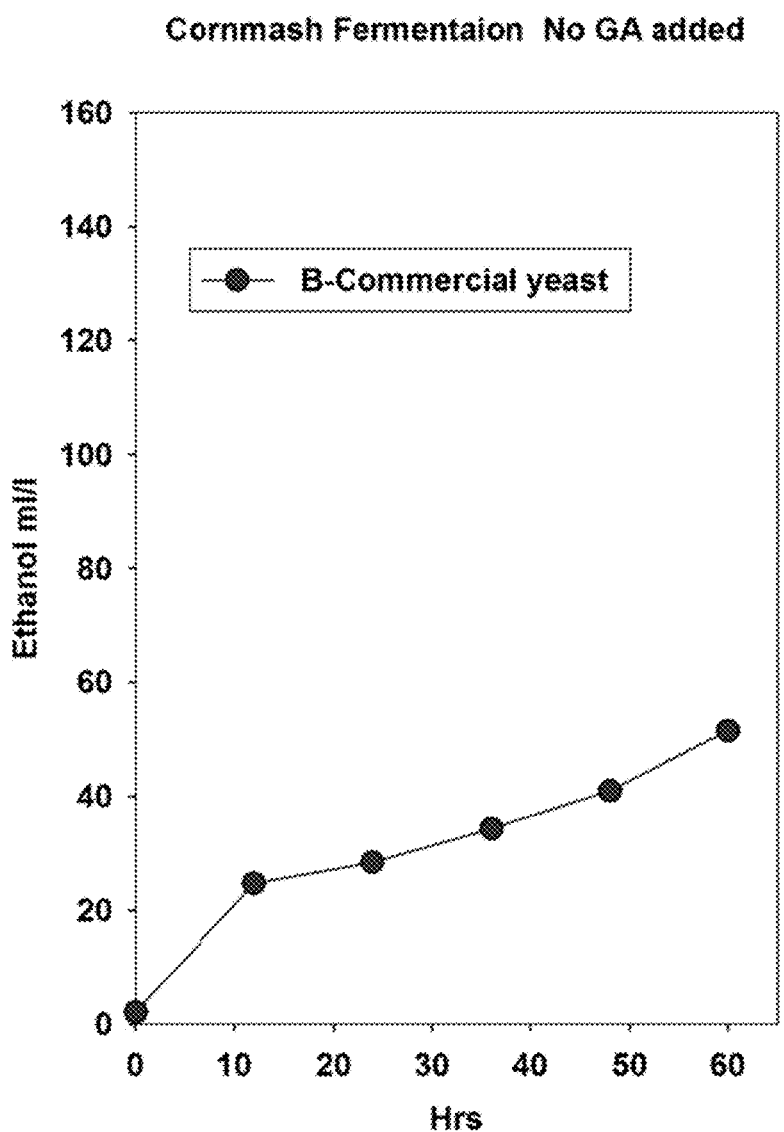
FIG. 5 is a graph that plots the production of ethanol over time via fermentation of corn mash by a commercial yeast strain without added glucoamylase.

Representative fermentation results are shown in FIGS. 3-5. For those yeast, for example the 424A(LNH-ST) yeast, also contain the externally cloned glucoamylase gene to produce glucoamylase, the enzymes produced by the cloned gene are usually to be secreted to the medium. The comparison of the glucoamylase activities being secreted by the 424A(LNH-ST) that only produces the natural yeast glucoamylase and the 424A(LNH-ST)-Gal yeast that contains both the natural yeast gene as well as the externally cloned glucoamylase gene is shown in FIG. 2 above. The 424A (LNH-ST)-Gal—yeast produces substantial more glucoamylase being secreted into the cultural medium than the original 424A(LNH-ST) yeast. However, the 424A(LNH-ST)-Gal does not contain too much more glucoamylase to produce glucose from corn mash to produce ethanol as shown in FIG. 3-5.

The secreted glucoamylase activity was measured using α-amylase treated soluble starch and at 37 Celsius. The glucose was assayed by Sigma glucose oxidase kit. The activity expressed as µg of glucose produced per min/ml culture from α-amylase treated soluble starch. For the GTA 424A(LNH-ST) strain with GA integrated, 55-60 µg/min/ml was expressed. For the original 424A(LNH-ST) strain that only contains the original glucoamylase expressed by the yeast SGA1 gene, the measurable glucoamylase activity corresponds to the expression of the SGA1 gene in 424A (LNH-ST) of about 2-4 µg/min/ml. For the commercial yeast strain, a much lower activity is anticipated relative to even the original strain.

Even though the GA integrated strain was found to exhibit more secreted activity compared to the original strain (424A) (LNH-ST), the ethanol yields of corn mash fermentation using the GA integrated strain was not too much more than the original 424A(LNH-ST). Both yeasts can produce 160 ml/l-170 ml/l ethanol in around 60 hrs. This demonstrates that the original 424A(LNH-ST) strain may provide nonnegligble amounts of glucoamylase for converting corn mesh or α-amylase treated soluble starch to ethanol.

In corn mash fermentation, the cells were grown in minimal medium where no rich nutrients was provided as nitrogen source. This minimal medium with corn mash makes the yeast grow somewhat slower. Nevertheless, even under this condition, both the original 424A(LNH-ST) and the strain containing additional GA integrated strain can both produce more than 16% ethanol in 60 hours or less. Besides, the GTA yeast may be adapted to the new culturing condition and can grow faster gradually. The culturing condition is designed for the selection those faster growing species all the time.

General Comments

Both the strain 424A(LNH-ST) and the strain 424A (LNH-ST)-GA are very stable and does not require special handling. The only consideration is that the seed cultural should be cultured under sterilized conditions and the medium should be properly prepared and sterilized as instructed.

Any container used with the 424A(LNH-ST) strain or the 424A(LNH-ST)-GA strain, including the small Eppendorf tubes, is better sterilized before being discarded or washed by any procedure to prevent the culture to be released and obtained by those not entitled to have such a yeast.

It is strongly recommended that any lab using recombinant yeast for glucosic and/or xylosic fermentation should purchase a Klett colorimeter and a couple dozens 300 ml flasks with a side arm. They make cell density measurements easier and more accurate, less time consuming, and less possibility to introduce contaminates into the culture.

Thus, a number of nonobvious aspects of the invention will be apparent upon inspection by a person having ordinary skill in the art in view of the disclosure contained herein. For example, the wild type yeast seems only to express its glucoamylase production gene during mating. Surprising, it has been found that an exemplary inventive diploid yeast, 424A(LNH-ST), that has always been cultured at vegetative state for many years now contains an functional SGA1 gene that can provide glucoamylase activity and may be used produce glucose from oligosaccharides. In turn, the yeast may ferment the glucose to ethanol. While the glucoamylase enzyme may not be secreted into the medium, the enzyme is or seems to be available to for degrading oligosaccharides or polysaccharides to glucose when those substrates (or feedstocks) are used.

In addition, additional GA gene has also been cloned into the 424A(LNHH-ST) yeast via gene cloning processes. Both the original yeast SGA gene as well as the 424A(LNH-ST) strain containing the external cloned GA (from *Aspergillus oryzae* species) can produce nonnegligible amounts of glucose from soluble starch that has been treated with α-amylase or from corn mash used by the American corn Ethanol Producers for the production of corn ethanol. It is believed that the yeast enzyme produced by the yeast endogenous gene may be attached either on the cell membrane or on the cell wall. As such, the enzyme is able to exhibit nonnegligible enzymatic activity to degrade the oligo saccharides present in corn mash that is corn starch being treated with steam, followed by the treatment with α-amylase to produce glucose for the yeast to ferment to ethanol.

Variations on the invention will be apparent to persons of ordinary skill in the art. For example, while inventive DNA may be located in a single species of microorganism, the invention may include more than one species. In such a case, microorganisms of differing species may exhibit similar culturing requirements so that they may be used to coferment glucosic and xylosic materials simultaneously. In addition, it is envisioned that the invention may employ a particular batch process, continuous process, or combination thereof to produce an organic compound of interest in purities of interest, i.e., in the absence of impurities of appropriate proportional ranges.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Similarly, while certain aspects of the invention have been actually reduced to practice, portions of the invention have been described in theoretical terms. The theoretical portions of the disclosure contained herein are not meant to be limiting. Furthermore, any numerical range set forth herein is to be interpreted in a manner such so as all numbers within the range is specifically called out. For example, recitation of a range from 1 to 2 includes recitations of 1, 2, 1.5, 1.1, 1.2, 1.3, 1.4, 1.5, 1.6, 1.7, 1.8, 1.9, 1.01, 1.001, 1001, 1.25, 1.75, etc.

All patents and publications referenced herein are incorporated by reference to the fullest extent practicable not inconsistent with the above disclosure. All claims below are to be construed as having the broadest, reasonable, and valid scope in all fora, e.g., all US courts and administrative agencies, all international courts and administrative agencies, and all other non-US national courts and administrative agencies.

What is claimed is:

1. In a container containing biomass, a microorganism capable of fermenting glucosidic and xylosic material to ethanol and also capable of expressing and/or secreting glucoamylase having nonnegligible enzymatic activity for breaking down polysaccharides of the biomass, the polysaccharides containing at least two six-carbon saccharidic units, wherein the microorganism is a 424A(LNH-ST) yeast, a 424A(LNH-ST)-GA yeast, or a 424A(LNH-ST)-Gal-GA yeast.

2. The microorganism of claim 1, wherein the biomass comprises edible plant matter.

3. The microorganism of claim 1, wherein the biomass comprises an inedible plant matter.

4. The microorganism of claim 1, wherein the biomass comprises corn mash.

5. The microorganism of claim 1, wherein the microorganism is a 424A(LNH-ST) yeast.

6. The microorganism of claim 1, wherein the microorganism is a 424A(LNH-ST)-GA yeast.

7. The microorganism of claim 1, wherein the microorganism is a 424A(LNH-ST)-Gal-GA yeast.

8. The microorganism of claim 1, capable of digesting corn.

* * * * *